(12) United States Patent
Pereira Da Silva et al.

(10) Patent No.: US 9,579,417 B2
(45) Date of Patent: Feb. 28, 2017

(54) GELLAN GUM SPONGY-LIKE HYDROGEL, ITS PREPARATION AND BIOMEDICAL APPLICATIONS THEREOF

(71) Applicant: ASSOCIATION FOR THE ADVANCEMENT OF TISSUE ENGINEERING AND CELL BASED TECHNOLOGIES AND THERAPIES—A4TEC, Braga (PT)

(72) Inventors: Lucilia Pereira Da Silva, Guimaraes (PT); Mariana Teixeira Cerqueira, Vila Nova de Gaia (PT); Rui Pedro Romero Amandi De Sousa, Matosinhos (PT); Alexandra Margarida Pinto Marques, Oporto (PT); Vitor Manuel Correlo Da Silva, Braga (PT); Rui Luis Goncalves Dos Reis, Oporto (PT)

(73) Assignee: ASSOCIATION FOR THE ADVANCEMENT OF TISSUE ENGINEERING AND CELL BASED TECHNOLOGIES AND THERAPIES-A4TEC, Braga (PT)

( * ) Notice: Subject to any disclaimer, the term of this patent is extended or adjusted under 35 U.S.C. 154(b) by 0 days.

(21) Appl. No.: 14/782,812

(22) PCT Filed: Apr. 9, 2014

(86) PCT No.: PCT/IB2014/060563
§ 371 (c)(1),
(2) Date: Oct. 7, 2015

(87) PCT Pub. No.: WO2014/167513
PCT Pub. Date: Oct. 16, 2014

(65) Prior Publication Data
US 2016/0325017 A1    Nov. 10, 2016

(30) Foreign Application Priority Data

Apr. 9, 2013 (PT) .......................... 106890

(51) Int. Cl.
| | |
|---|---|
| A61L 27/20 | (2006.01) |
| A61L 27/56 | (2006.01) |
| A61L 27/52 | (2006.01) |
| A61L 27/54 | (2006.01) |
| A61L 27/12 | (2006.01) |
| A61L 27/38 | (2006.01) |
| A61L 27/26 | (2006.01) |

(52) U.S. Cl.
CPC ............. *A61L 27/20* (2013.01); *A61L 27/12* (2013.01); *A61L 27/26* (2013.01); *A61L 27/3804* (2013.01); *A61L 27/3834* (2013.01); *A61L 27/52* (2013.01); *A61L 27/54* (2013.01); *A61L 27/56* (2013.01); *A61L 2300/112* (2013.01); *A61L 2300/216* (2013.01); *A61L 2300/252* (2013.01); *A61L 2300/414* (2013.01); *A61L 2300/428* (2013.01); *A61L 2400/18* (2013.01); *A61L 2430/02* (2013.01)

(58) Field of Classification Search
CPC ........ A61K 8/73; A61K 8/042; A61K 9/5036; A61K 9/1652
See application file for complete search history.

(56) References Cited

U.S. PATENT DOCUMENTS

| | | |
|---|---|---|
| 7,147,885 B2 | 12/2006 | Asano et al. |
| 2007/0031499 A1 | 2/2007 | Huh et al. |
| 2009/0291115 A1 | 11/2009 | Gemeinhart |

FOREIGN PATENT DOCUMENTS

| | | |
|---|---|---|
| WO | 2006037606 A2 | 4/2006 |
| WO | 2009101518 A2 | 8/2009 |

OTHER PUBLICATIONS

International Search Report dated Jul. 29, 2014 for PCT/IB2014/060563 and Written Opinion.

*Primary Examiner* — Kyle Purdy
(74) *Attorney, Agent, or Firm* — Lucas & Mercanti, LLP

(57) ABSTRACT

The present application discloses cell-adhesive gellan gum spongy-like hydrogels that are able to entrap/encapsulate adherent cells, which spread within the material, maintaining their phenotype and remaining viable and proliferative. The methodology used to obtain these materials involves hydrogel preparation, freezing, freeze-drying and re-hydration with a saline solution with cells and with/without bioactive molecules. No pre and/or post functionalization of the spongy-like hydrogels with cell adhesive features, as used for other hydrogels, is used. The cell adhesive character of these materials, not observed in hydrogels, is in part explained by their physical properties, between sponges and hydrogels, dissimilar from the precursor hydrogels. The physical properties that are mainly different are the morphology, microstructure, water content, and mechanical performance. Gellan gum spongy-like hydrogels physical properties and biological performance can be tuned by manipulating the parameters involved in spongy-like hydrogel formation. Bioactive molecules can also be entrapped with or without cells to modify the biological performance of the spongy-like hydrogels. These materials can be applied in the context of bioengineering, tissue engineering, regenerative medicine and biomedical applications.

23 Claims, 10 Drawing Sheets

GELLAN GUM SPONGY-LIKE HYDROGEL, ITS PREPARATION AND BIOMEDICAL APPLICATIONS THEREOF

CROSS REFERENCE TO RELATED APPLICATION

This Application is a 371 of PCT/IB2014/060563 filed on Apr. 9, 2014 which, in turn, claimed the priority of Portuguese Patent Application No. 106890 filed on Apr. 9, 2013, both applications are incorporated herein by reference.

TECHNICAL FIELD

The present application relates to a cell-adhesive gellan gum material, its method of preparation and biomedical applications thereof.

BACKGROUND

Gellan gum is a bacterial exopolysaccharide of natural origin prepared by aerobic submerged fermentation of *Sphingomonas elodea*. Gellan gum is a linear and anionic polymer composed of repeating units of a tetrasaccharide (1,3-β-D-glucose, 1,4-β-D-glucuronic acid, 1,4-β-D-glucose, 1,4-α-L-rhamnose), similar to the glycosaminoglycans existing in the extracellular matrix.

Gellan gum hydrogels can be formed by two different ways: by temperature decrease lower critical solution, and by the addition of ions. Hence, gellan gum hydrogels are termed thermoreversible hydrogels as they respond to temperature decrease with a sol-gel transition. In fact, gellan gum has a thermally reversible coil form at high temperatures which upon temperature decrease, changes to double-helix that anti-parallel self-assemble in the form of oriented bundles. These, called junction zones that per se link untwined regions of extended helical chains, lead to the formation of a three dimensional network, the hydrogel. In addition, the use of counterions, specifically monovalent or divalent cations, promotes a physical bonding between cations and carboxylate groups of the gellan gum, particularly strong when involving divalent ions, leading to the formation of the three dimensional and reticulated hydrogel. Due to this dual formation mechanism, gellan gum hydrogels have great potential for biomedical applications because they can gellify in situ in vivo.

WO Patent 2009/101518 A2 from 20 Aug. 2009 discloses for the first time the use of gellan gum hydrogels for regenerative medicine and tissue engineering applications, the system, and processing devices. It refers the possibility of using cell/bioactive agents within hydrogels, by including these components while homogenizing the matrix along the gelation. Accordingly, gellan gum hydrogels are particularly attractive to tissue engineering because of their possibility to encapsulate cells/biochemical molecules. Similarly to what happens in most of cell niches of the majority of tissue engineering applications, cells in hydrogels should attach, form focal contacts and organize their own cytoskeleton to spread and to be able to proliferate. However, hydrogels, including gellan gum hydrogels, hardly present cell adhesion properties as they lack cell anchorage points and/or are highly hydrophilic promoting water molecules bounding to the polymer backbone, thus inhibiting cell adhesion (Chang and Wang 2011). Furthermore, most of the hydrogels are composed of negatively charged polymers, known to repulse negatively charged cells and to limit the adsorption of cell adhesive proteins. To overcome this cell adhesion limitation, different approaches have been proposed. One of the strategies used includes the incorporation, within the polymeric matrix, of extracellular matrix (ECM) molecules, such as collagen, thrombospondin, osteopontin, fibronectin and vitronectin, which are known to promote cell adhesion. Moreover, the improvement of the adsorption of fibronectin and vitronectin glycoproteins to the polymer backbone, as well as other proteic components of serum, routinely used for cell culture, has been another approach used to improve cell adhesion to hydrogels (von der Mark, Park et al. 2010; Chang and Wang 2011). Similarly, peptide sequences, namely RGD, IKVAV or YIGSR, present on those glycoproteins, have been incorporated into the backbone of polymers, by chemical modification prior to the formation of the hydrogels. In fact, US Patent 2007/A1 from 19 Jul. 2009 discloses the use of RGD peptide sequence to promote the adhesion of cells within hydrogels. The use of proteins from animal sources introduces immunogenicity and disease transmission concerns that from a clinical perspective and from the regulatory point of view might never be overcome. Additionally, polymer modifications with proteins and/or peptides sequences are not only time-consuming but also implicate significant costs associated with the use of recombinant bioactive molecules.

The gellan gum dried polymeric structures (xerogels) quickly gain spongy-like hydrogel properties after re-hydration, not observed in either hydrated xerogels (US Patent 2007/0031499 A1), hydrated lyophilized gellan gum hydrogels (U.S. Pat. No. 7,147,885 B2), or hydrated xerogel/film comprising cellulose ether and gellan gum (WO Patent 2006/037606 A2). These patents make no reference to the use of cells and/or bioactive molecules.

US Patent 2007/0031499 A1 from 8 Feb. 2009 discloses the use of xerogels and the incorporation of pharmaceuticals while preparing the hydrogels. No reference is made to the re-hydration of the xerogels, with the use of cells or/and bioactive agents. Authors refer the inclusion of pharmaceuticals in xerogels with techniques to maintain the dryness of the xerogel and not in its hydrated state. Due to the drying processing conditions that might be harsh, the properties of the drugs can be altered. In the present invention the drugs and/or bioactive molecules are incorporated in the dried polymeric networks (xerogels) after freeze-drying, at the time of re-hydration, avoiding chemical alterations affecting its activity. This patent makes no reference to the use of cells and/or bioactive molecules.

U.S. Pat. No. 7,147,885 B2 from 12 Dec. 2006 discloses the use of native gellan gum, based on its multifunctionality, like in food. The patent also refers that dehydrated gels and jellies can be prepared from gels of gellan gum, by hot air current or freeze-drying. However, when water is added to this dehydrated hydrogel (dehydrogel) and the mixture is allowed to stand, the dehydrogel readily absorbs a large amount of water and swells depicting physical properties not much different from the properties of the original hydrogel prior drying. In the present invention, the spongy-like hydrogels, the dried structure after the re-hydration, accomplish physical properties dissimilar from the previous precursor hydrogels. This patent makes no reference to the re-hydration of the lyophilized hydrogels with cells and/or bioactive molecules.

WO Patent 2006/037606 A2 from 13 Apr. 2006 discloses the use of a xerogel/film comprising cellulose ether and gellan gum that can be used as a dry storage form of the gel or as a hydrogel after hydration with an aqueous solution that can be loaded with active ingredients for controlled rate, or in contact with aqueous body fluids. Again, the hydrated xerogel, as described by the authors "swell and form hydrogels when in contact with aqueous solutions", maintaining the same properties observed on the precursor hydrogels. Spongy-like hydrogels have different physical properties relatively to hydrogels, in terms of morphology, microstructure, and mechanical properties. Spongy-like hydrogels have higher porosity, pore size and thicker pore walls, lower water content, higher physical stability and flexibility that results in a cell-adhesive character. Moreover, WO Patent 2006/037606 A2 claims the use of the mixture of both cellulose ether and gellan gum that "synergistically combine their benefits and complement one another to prevent their disadvantages observed when used alone". In the present, we attain the main physical properties of spongy-like hydrogels only by using gellan gum, although other polymers can also be used along with gellan gum. This patent makes no reference to the re-hydration of the lyophilized hydrogels with cells.

The manuscript entitled "In vitro properties of gellan gum sponge as the dental filling to maintain alveolar space" from Chang et al. 2012 describes a dried gellan gum sponge prepared by the subsequent steps of gellan gum dissolution, freeze-drying, post chemical crosslinking, and finally freeze-drying. Chang et al. 2012 work only potentiate the use of the sponges in its dried state. No reference is made to the re-hydration of the gellan gum sponges with cells and/or bioactive molecules.

The fast water uptake and mechanical stability of gellan gum spongy-like hydrogels observed after its re-hydration was only similarly observed in superporous hydrogels (US 2009/0291115 A1).

US Patent 2009/0291115 A1 from 26 Nov. 2006 discloses the method of superporous hydrogel formation, which requires the addition of foaming agents while being processed, and the possibility of incorporating viable cells while preparing the hydrogel. Nevertheless, the cell performance, such as cell adhesion, was not referred. Gellan gum spongy-like hydrogels do not need any additional polymer/agent and crosslinking agent/condition to create the final polymeric architecture that enables a fast water uptake, mechanical stability and improved cell seeding, viability, adhesion, proliferation and differentiation.

WO Patent 2009/101518 A2 from 20 Aug. 2009 discloses the use of gellan gum hydrogels for regenerative medicine and tissue engineering applications, the system, and processing devices. No reference is made to the rehydration with cells and/or bioactive molecules.

SUMMARY

Cell adhesive gellan gum material is prepared from a gellan gum hydrogel after freezing, freeze-drying and re-hydration, without using pre or post-functionalization.

This material comprises different and tunable physical, morphological, mechanical and biological properties relatively to the precursor hydrogel and allows the adhesion of cells that exhibit their typical phenotype and the entrapment/encapsulation of bioactive molecules.

This material can be applied in the context of bioengineering, tissue engineering, regenerative medicine and biomedical applications, like drug deliver and tissue regeneration and engineering and repair of skin and connective tissues Thus the present disclosure describes a cell-adhesive gellan gum material, which is a spongy-like gellan gum hydrogel with a pore diameter between 10 µm and 900 µm, and a mean pore size diameter between 200 µm and 600 µm, a pore wall thickness ranging between 50 µm and 100 µm and a water content between 1000 and 2500% (w/w).

A preferred embodiment of the present invention, the spongy-like gellan gum hydrogel presents a capacity recovery from 60-80% of deformation in 5-15 min and 90-100% of recovery after 3 hours.

In another embodiment of the present invention, the cells entrapped and adhered to the cell-adhesive gellan gum material maintain their phenotype.

A preferred embodiment of the present invention, bioactive molecules are entrapped in the cell-adhesive gellan gum material.

It is also an objective of the present invention to describe the method for producing the cell-adhesive gellan gum material comprises the following steps:
  hydrogel preparation;
  freezing, for water and salt cold crystallization;
  freeze-drying, to remove all water;
  re-hydration with a solvent or solution.

A preferred embodiment of the present invention, after the hydrogel preparation, the same is stabilized in a saline solution.

In another embodiment of the present invention, the gellan gum is selected from a group comprising low-acyl gellan gum, high-acyl gellan gum, chemically modified gellan gum, or any mixture of these gellan gum polymers.

A preferred embodiment of the present invention, the gellan gum is used in combination with other molecules including:
  organic molecules selected from a group comprising polymers of natural or synthetic origin, chemically modified or co-polymers, such as hyaluronate, chitosan, collagen, polyethyleneglicol and fibrinogen, such as peptides, proteins, lipids, polysaccharides;
  inorganic molecules selected from a group comprising bioactive glass, hydroxyapatite, calcium phosphate and iron.

In another embodiment of the present invention, the gellan gum is used in different amounts, from 0.1% (w/v) to 10% (w/v).

A preferred embodiment of the present invention, the hydrogel preparation comprises the dissolution of gellan gum in a solvent and reticulation by a crosslinking mechanism.

In another embodiment of the present invention, the solvent comprises water, phosphate buffer solution (PBS), saline solution or cell culture medium.

A preferred embodiment of the present invention, the dissolution of gellan gum occurs at temperatures above polymer(s) critical gelling temperature, preferably at 90° C. and for 10 to 30 minutes.

In another embodiment of the present invention, the crosslinking mechanism for reticulation comprises mixing the dissolved gellan gum with a reticulation agent, including ions and decreasing the temperature below the polymers critical gelling temperature.

A preferred embodiment of the present invention, freezing is performed during 1 hour to 1 year, more preferably, during 12 to 44 hours.

In another embodiment of the present invention, freezing is performed at a temperature between −4° and −196° and at different cooling ratios from 0.1° C. per minute to 20° C. per minute.

A preferred embodiment of the present invention, the temperature is unaltered during freezing.

In another embodiment of the present invention, freeze-drying is performed for one cycle, at −80° C. and at 0 atm, for 6 hours to 15 days, preferably for 3-7 days.

A preferred embodiment of the present invention, rehydration is performed with a polar solvent including water, simulated body fluids (SBF), phosphate buffer solution (PBS) or cell culture medium.

In another embodiment of the present invention, rehydration is performed with cell culture medium.

A preferred embodiment of the present invention, rehydration is performed with one or more types of cells selected from a group comprising cell lines, primary cells, progenitor cells and stem cells, including human adipose stem cells (hASCs) and microvascular endothelial cells (hAMECs).

In another embodiment of the present invention, rehydration is performed with one or more types of bioactive molecules selected from a group comprising growth factors, antibodies, antibiotics, anti-microbial, anti-fungi, antimicotics, anti-inflammatory factors, enzymes, metallic elements, growth hormone, cytokines, interleukins, chemokines, angiogenic factors, anti-angiogenic factors, anti-coagulants, contrasting agents, chemotherapeutic agents, signaling pathway molecules, cell receptors, and cell ligands.

It is also an objective of the present invention to describe the use of the cell-adhesive gellan gum material in biomedical applications, including drug deliver and tissue regeneration and engineering and repair of skin and connective tissues.

GENERAL DESCRIPTION

The present application presents a gellan gum spongy-like hydrogels that are able to entrap/encapsulate and support the adhesion of adherent cells, which spread within the material, maintaining their typical phenotype and remaining viable and proliferative.

The methodology used to obtain gellan gum spongy-like hydrogels involves hydrogel preparation, freezing, freeze-drying and re-hydration with a solvent/solution with/without cells and with/without bioactive molecules.

No pre and/or post functionalization with cell adhesive features, as previously enounced for other hydrogels, is made to prepare spongy-like hydrogels.

The cell adhesive character of gellan gum spongy-like hydrogels, not observed in hydrogels, is in part explained by their physical properties, between sponges and hydrogels, but dissimilar from the precursor hydrogels.

The physical properties that are mainly different are the morphology; microstructure, such as porosity, pore size and pore wall thickness; water content; mechanical performance such as visco-elasticity, stiffness, physical stability, flexibility and recovery capacity.

The physical properties of spongy-like hydrogels and, per se, their biological performance, can be tuned by simply manipulating the parameters involved in spongy-like hydrogel formation.

The parameters that can be varied are, but not limited to, the type and amount of the polymer(s), the type and amount of crosslinker(s), the type and composition of the solvent, and the use of ions/salts used in the preparation of hydrogels; the freezing conditions (type, temperature, time); the freeze-drying conditions (time, temperature, pressure, number and time of cycles).

The physical properties that can be varied include, but are not limited to, morphology, microstructure, shape, visco-elasticity, stiffness, water absorption and content, protein adsorption, brittleness, ductility, elasticity, fluidity, viscosity, permeability, plasticity, physical stability, and flexibility.

The biological performance that can be varied or improved include, but is not limited to, cells viability rate, proliferation, adhesion, spreading, differentiation and signaling of the encapsulated/entrapped adherent cells.

The use of bioactive molecules within the spongy-like hydrogels allow modulating the biological performance of the materials by conferring functionalities that affect tissue repair and regeneration including, but not limited to, inflammation, angiogenesis, matrix remodeling.

The patent here proposed innovates in some distinct and fundamental aspects from others.

BRIEF DESCRIPTION OF THE DRAWINGS

Without intent to limit the disclosure herein, this application presents attached drawings of illustrated embodiments for an easier understanding.

202—hydrogel; and
203—spongy-like hydrogel.

Figure 1:
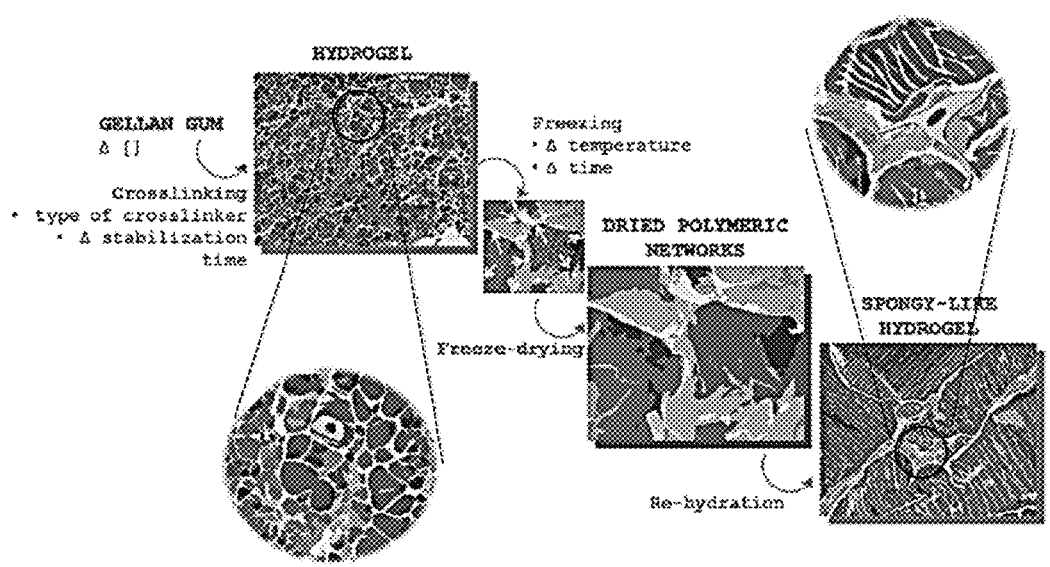
FIG. 1: Illustrates a scheme of the processing methodology to obtain spongy-like hydrogels from precursor hydrogels (From gellan gum hydrogel to dried polymeric networks to spongy-like hydrogels, through hydrogel preparation and polymer network stabilization in a saline solution, freezing, freeze-drying and re-hydration with cells and with/without bioactive molecules) and illustrates cell spreading within the materials.
Figure 2:
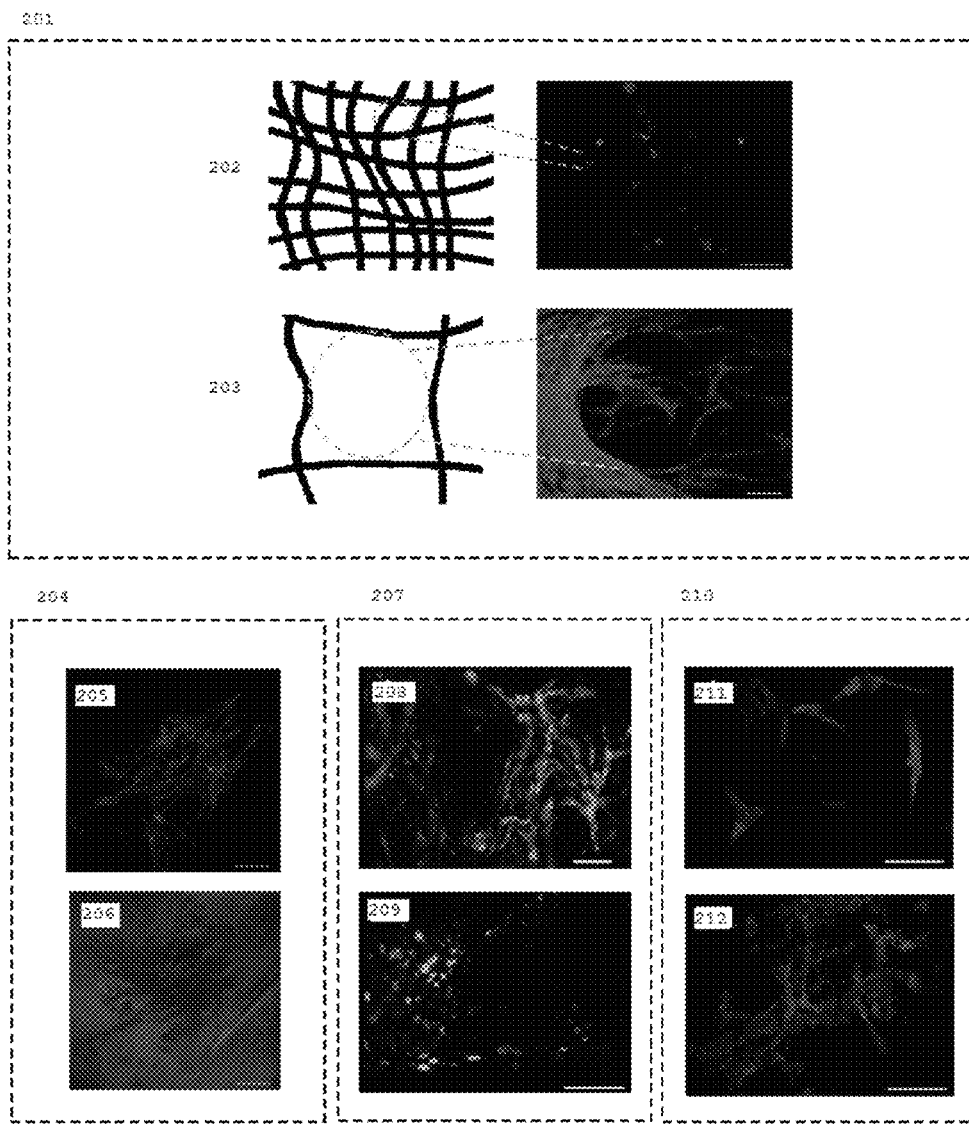
FIG. 2: Shows (201) schematic representation of hydrogel and spongy-like hydrogel polymeric network microstructure (left) and fluorescence microscopy images of human adipose stem cells (hASCs) cytoskeleton within GG 1.25% hydrogels and spongy-like hydrogels, after Phalloidin-TRITC staining (red) (right). (204) Cell-adhesive character of hASCs within GG 1.25% spongy-like hydrogels. (205) Confocal microscopy of hASC attachment and spreading, after Phalloidin-TRITC staining (red) and (206) respective cell shape imprinting after 14 days of cell culture. (207) Viability and proliferative state of hASCs within GG 1.25% spongy-like hydrogels, after 14 days of cell culture. (208) Fluorescence microscopy of dead (red) and live (green) cells, respectively stained with propidium iodide (PI) and calcein AM, and (209) expression of Ki-67 marker, indicative of their proliferative state. (210) Influence of serum in hASC adhesive character within GG 1.25% spongy-like hydrogels, after 3 days of culture. Fluorescence microscopy images of hASC cytoskeleton after Phalloidin-TRITC staining (red) in (211) complete medium and (212) medium without serum. Cells nuclei were stained with DAPI (blue). Scale bar=100 μm. 1—Hydrogel; 2—Spongy-like hydrogel. The reference numbers show.
Figure 3:
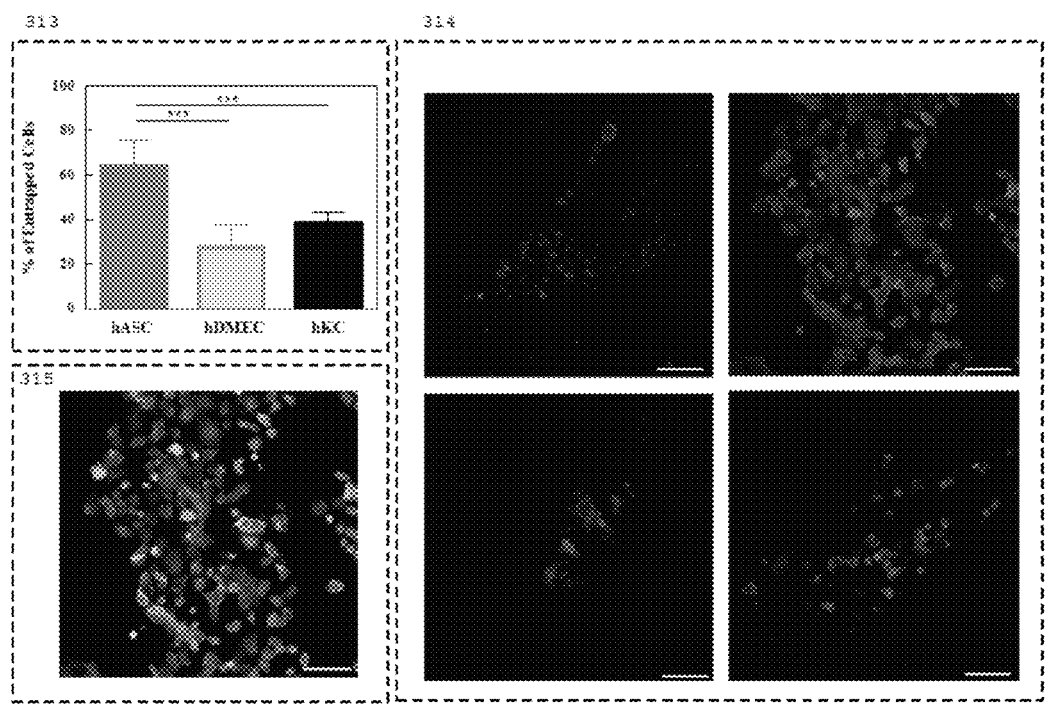

FIG. 3: Illustrates gellan gum spongy-like hydrogel adhesive character dependence with cells specificities. (313) Representation of hASCs, human dermal microvascular endothelial cells (hDMECs) and human keratinocytes (hKCs) entrapment efficiency within GG 1.25% spongy-like hydrogels determined by double stranded DNA quantification after 24 h of culture. (314) Representative confocal microscopy images of hKC (top) and osteoblast-like cells SaOs-2 (bottom), after Phalloidin-TRITC staining (red), within GG 1.25% hydrogels (left) and spongy-like hydrogels (right) after 14 days of cell culture showing cells cytoskeleton organization due to adhesion. (315) Representative fluorescence microscopy image of hKC, after Keratin 14 (green) and Phalloidin-TRITC staining (red), in GG 1.25% spongy-like hydrogels confirming the phenotype maintenance of hKCs. Scale bar=100 μm.

Figure 4:
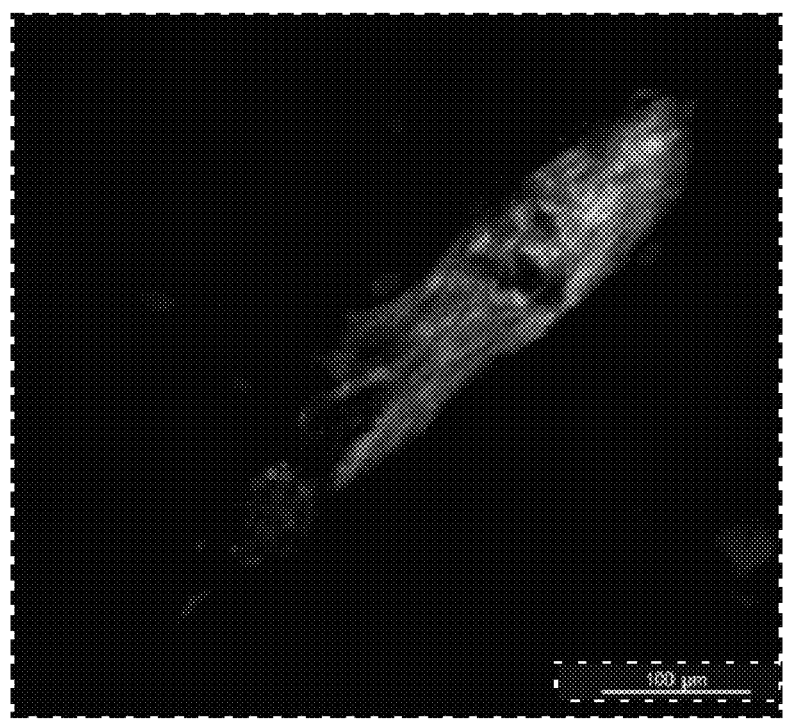

FIG. 4: Illustrates zonal cell seeding of human dermal endothelial cells (hDMECs) and human dermal fibroblasts (hDFb) within a specific and confined area of GG spongy-like hydrogels. hDMECs were marked with the endothelial cell marker DiI AcLDL (red), hASC and hDFbs were marked with the viability marker calcein (green). Nuclei were stained with DAPI (blue). Scale bar=100 μm.

Figure 5:
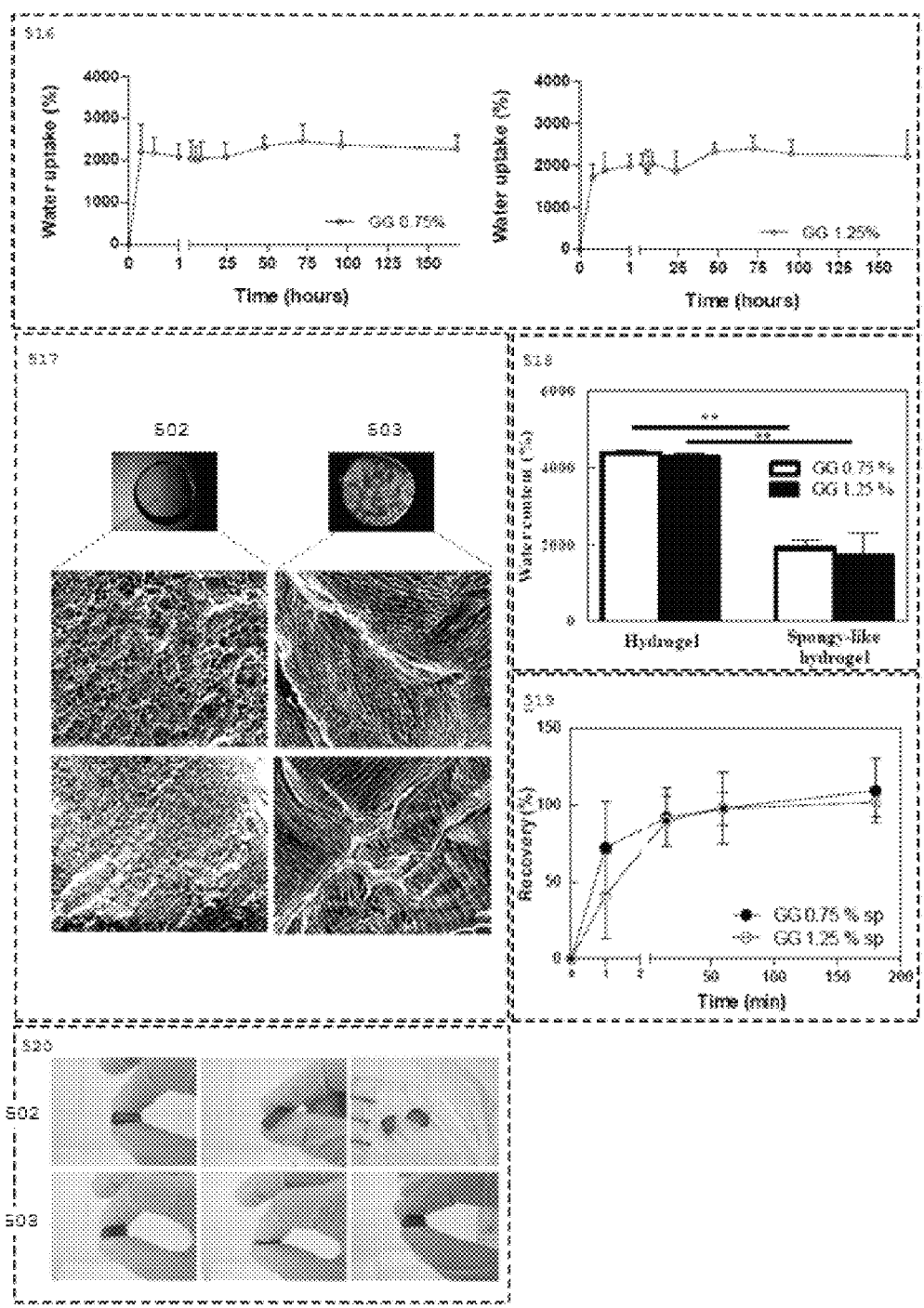

FIG. 5: Illustrates the physical properties of GG hydrogels and respective spongy-like hydrogels confirming the differences between them. (516) Water uptake profile of dried polymeric networks along 7 days of immersion in PBS. (517) Macroscopic appearance and cryo-SEM representative micrographs of hydrogels and spongy-like hydrogels of GG 0.75% (w/v) (top) and GG 1.25% (w/v) (bottom) microstructure, showing pore wall lineament (blue). (518) Water content of hydrogels and spongy-like hydrogels. (519) Sequential macroscopic demonstration of hydrogel brittle character in contrast to spongy-like hydrogel ductility during the deformation process. (520) Recovery capacity of spongy-like hydrogels after compressive force deformation. The reference numbers show:

502—hydrogel; and
503—spongy-like hydrogel.

Figure 6:
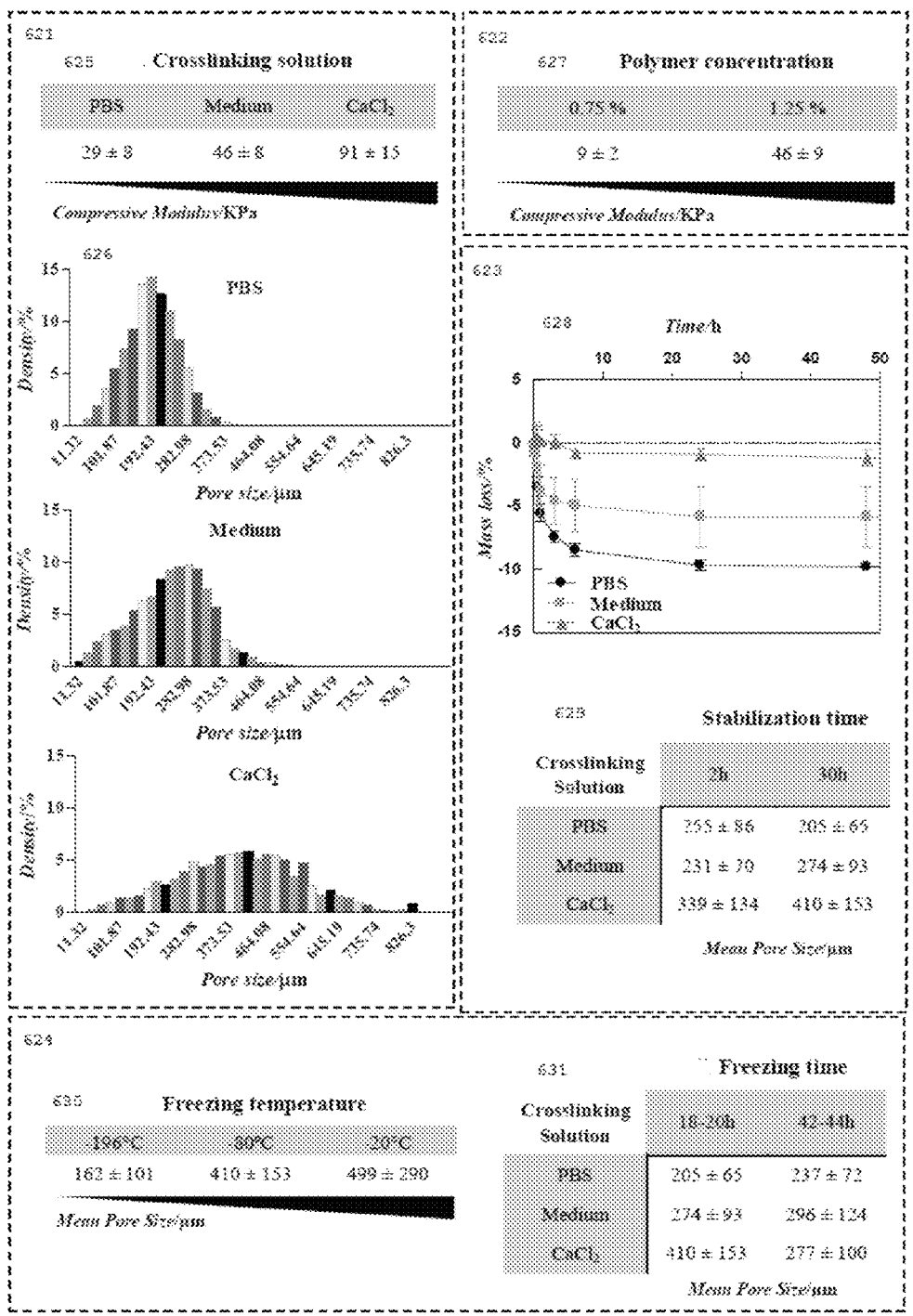

FIG. 6: Shows the effect of (621) crosslinking solution, (622) polymer concentration, (623) stabilization time during hydrogel formation, (624) hydrogel freezing temperature and time on gellan gum spongy-like hydrogels physical/mechanical properties. (625) Compressive modulus of GG 1.25% hydrogels crosslinked with PBS, cell culture medium and $CaCl_2$ confirming the influence of the crosslinking solution over the stiffness of the hydrogels. (626) Pore size spectra of dried polymeric networks obtained from GG 1.25% hydrogels crosslinked with PBS, cell culture medium and $CaCl_2$ frozen for 18-20 h, confirming the influence of the crosslinking solution over the pore size distribution of the dried polymeric networks, determined by X-Ray Microtomography. (627) Compressive modulus of GG 0.75% and GG 1.25% hydrogels crosslinked with cell culture medium, demonstrating the direct correlation between the concentration of polymer and the stiffness of the hydrogels. (628) Representation of the percentage of mass loss of GG 1.25% hydrogels crosslinked with PBS, cell culture medium and $CaCl_2$, along the 48 h stabilization period in PBS. (629) Effect of the stabilization time in PBS of GG 1.25% hydrogels crosslinked under different conditions, over the mean pore size of the respective dried polymeric networks, determined by X-Ray Microtomography. (630) Effect of freezing temperature over the mean pore size and microstructure of dried polymeric networks obtained from GG 1.25% hydrogels crosslinked with $CaCl_2$, determined X-Ray Microtomography. (631) Effect of freezing time of GG 1.25% (w/v) hydrogels crosslinked under different conditions, over the mean pore size of the respective dried polymeric networks, determined by X-Ray Microtomography.

Figure 7:
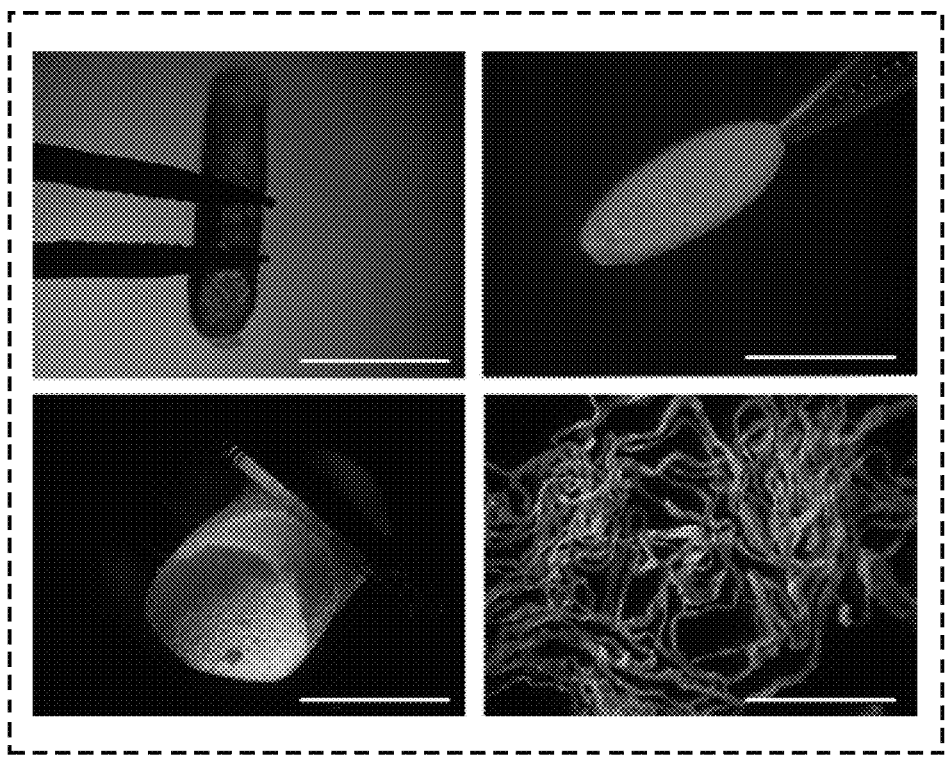

FIG. 7: Illustrates the processing versatility of GG spongy-like hydrogels. Dried polymeric networks can be prepared with different shapes according to the intended regenerative medicine application. Scale bar=10 mm.

Figure 8:
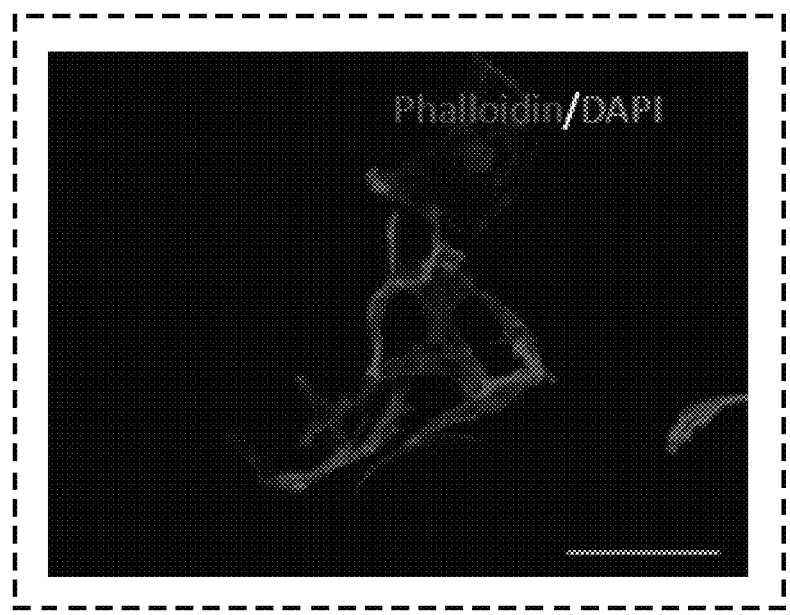

FIG. 8: Illustrates hASC morphology within GG 1.25% (w/v) spongy-like hydrogels, formed from the dried polymeric networks stored off-the-shelf, for a period of 12 months. A representative fluorescence microscopy image of hASCs morphology within GG 1.25% (w/v) spongy-like hydrogels, after 3 days of culture, and after Phalloidin-TRITC staining (red). Nuclei were stained with DAPI (blue). Scale bar=100 μm.

Figure 9:
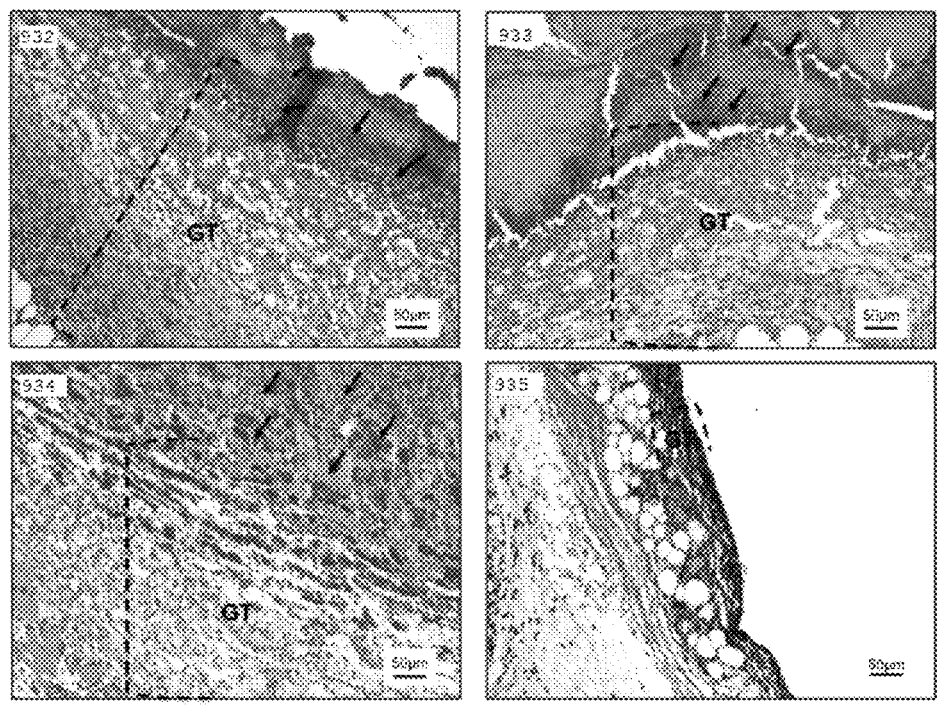

FIG. 9: Shows tissue reaction 3 days after transplantation of (932) gellan gum/hyaluronic acid spongy-like hydrogel (933) gellan gum/hyaluronic acid spongy-like hydrogels with human adipose stem cells and (934) gellan gum/hyaluronic acid spongy-like hydrogels with human adipose stem cells and human adipose microvascular endothelial cells, in full-thickness excisional wounds in nude mice. (935) Represents the control condition, just containing PBS. The histological analysis of the explants stained with H&E revealed the absorption of the exudates by the spongy-like hydrogels (arrows) and significant granulation tissue (GT, limited by the dashed line) formation in the experimental conditions (932-934) in comparison to the control (935).

Figure 10:
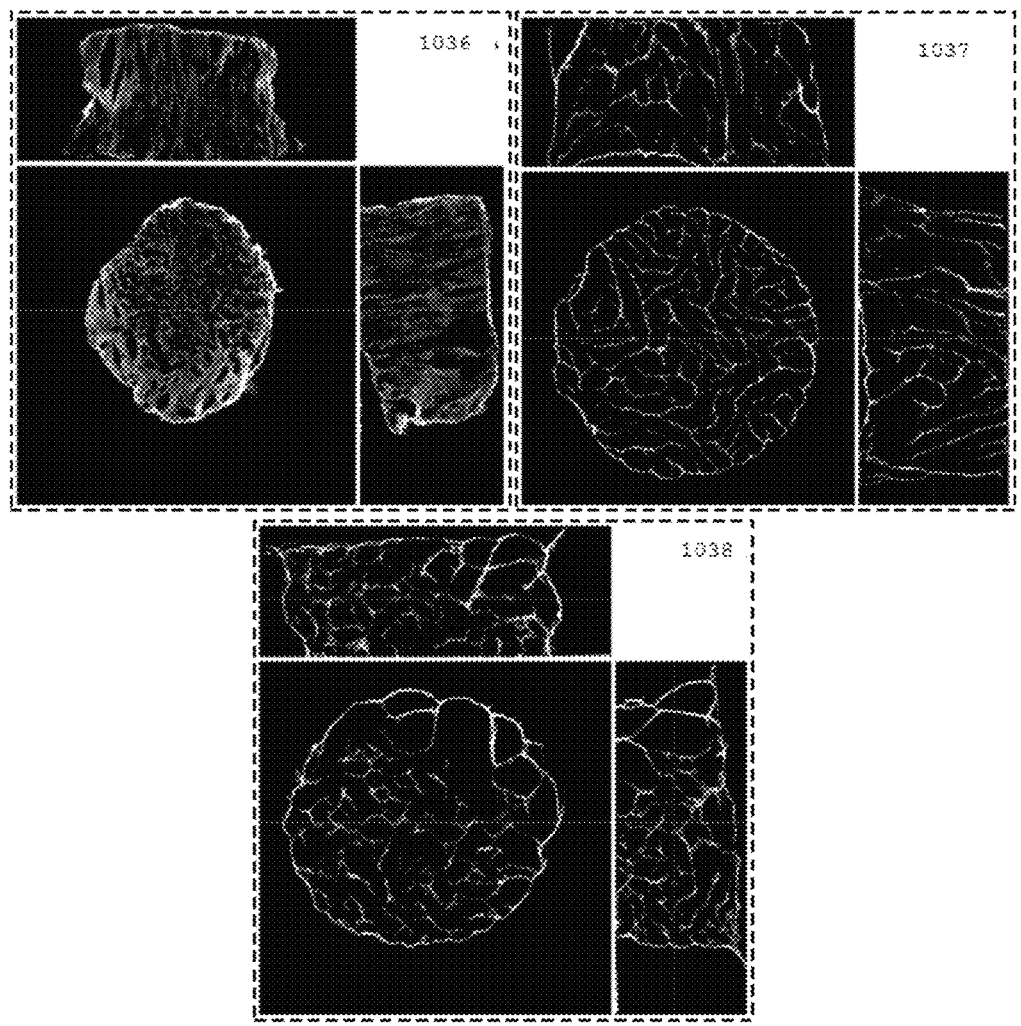

FIG. 10: Shows the distinct microstructure of GG 1.25% (w/v) spongy-like hydrogels frozen at different freezing conditions, obtained by X-Ray Microtomography. (1036) –196° C. Freezing temperature by using liquid nitrogen (1037) –80° C. Freezing temperature (1038) –20° C. Freezing temperature.

DESCRIPTION OF THE EMBODIMENTS

Referring to the drawings, herein are described optional embodiments in more detail, which however are not intended to limit the scope of the present application.

The following definitions serve to clarify and understand some of the terminologies used in the description of this patent. The exceptions to these definitions are defined along the text.

The terminology "hydrogel" as used herein refers to network structures of crosslinked polymers with hydrophilic groups or domains that confer the hydrogels the capability to absorb and retain a high content of water, acquiring a visco-elastic character and facilitating the transport of oxygen, nutrients and waste.

The terminology "sponge" as used herein refers to porous scaffolds, with high capability of absorbing water, and highly elastic.

The terminology "dried polymeric networks" as used herein refers to dried structures, after hydrogel preparation, freezing and freeze-drying.

The terminology "spongy-like hydrogels" as used herein refers to re-hydrated dried-polymeric networks with a solvent/solution with/without cells and with/without bioactive molecules. "Spongy-like hydrogels" present characteristics of sponges and hydrogels.

The terminology "gellan gum material" as used herein, unless described otherwise, refers to any structure prepared with gellan gum, alone or in combination with other natural/synthetic/modified polymer(s) or co-polymer(s), peptides, proteins, lipids, and polysaccharides, not excluding other molecules. Gellan gum includes, but is not limited to, low-acyl gellan gum, high-acyl gellan gum, chemically modified gellan gum, or any mixture of these gellan gum polymers. Other natural/synthetic/modified polymer(s) or co-polymer(s) includes, but is not limited to, hyaluronate, chitosan, collagen, polyethylene glycol and fibrinogen.

The terminology "xerogel" as used herein refers to the dried structures obtained after drying hydrogels.

The term "physical properties" as used herein is any property that is measurable and which the value designates the state of a physical system. Physical properties include, but are not limited to, morphology, microstructure, shape, visco-elasticity, stiffness, water absorption, protein adsorption, brittleness, ductility, elasticity, fluidity, viscosity, permeability, plasticity, physical stability, and flexibility.

The term "biological performance" as used herein refers to the cellular activity that includes, but is not limited to, cell viability, proliferation, adhesion, spreading, differentiation, signaling, and tissue repair and regeneration including processes such as, but not limited to, inflammation, angiogenesis, matrix remodeling.

The terminology "bioactive molecules" as used herein refers to any molecule that has any beneficial or adverse effect on a cell, tissue or living organism. The molecules include, but are not limited to, growth factors, antibodies, antibiotics, anti-microbial, anti-fungi, antimicotics, anti-inflammatory factors, enzymes, metallic elements, growth hormone, cytokines, interleukins, chemokines, angiogenic factors, anti-angiogenic factors, anti-coagulants, contrasting agents, chemotherapeutic agents, signaling pathway molecule, a cell receptor, and cell ligand.

Other terminologies, such as all technical and scientific terms used herein, were previously described by others and have the same meaning. This terminology is commonly understood by someone who is in the scientific field of the present invention.

This application is not limited to the particular embodiments herein described. The embodiments only serve as examples and may vary. This terminology describes particular embodiments only, and is not a limitation of this invention, as the limitations are only made by the claims.

The range of values that are used in the present invention include a lower, an upper limit and all the intervening values. Ranges excluding, one or both of these limits are also included in the present invention, and ranges excluding one or more of the intervening values are also included in the present invention. The intervening value includes the tenth of the unit of the lower and upper limit, the value between the upper and lower limit of the range, and any other stated or intervening value the range. The upper and lower limits of these smaller ranges may independently be included in the smaller ranges, and are also encompassed within the invention, subject to any specifically excluded limit in the stated range.

The present invention can be reproduced using other similar materials and methodologies. Meanwhile, the materials and methods used for the present invention are herein described. All publications mentioned herein are incorporated by reference to disclose and describe the methods and/or materials in connection with which the publications are cited.

The singular forms "a," "an," and "the" include plural referents unless the context clearly dictates otherwise. For example, reference to "a hydrogel" includes a plurality of such hydrogels and reference to "the polymer" includes reference to one or more polymers and equivalents.

Gellan gum spongy-like hydrogels are able to entrap/encapsulate adherent cells, which spread within the material, maintaining their phenotype and remaining viable and proliferative.

The cell adhesive character of gellan gum spongy-like hydrogels, not observed in hydrogels, is in part explained by their physical properties, between sponges and hydrogels, dissimilar from the precursor hydrogels.

The physical properties that are mainly different are the morphology, microstructure, such as porosity and pore size; water content; mechanical performance such as the viscoelasticity, the stiffness, the physical stability, and flexibility.

The spongy-like gellan gum hydrogel characterized in that it has a pore diameter between 10 µm and 900 µm, and a mean pore size diameter between 200 µm and 600 µm; the pore wall thickness ranges between 50 µm and 100 µm and a water content between 1000 and 2500%, determined by the difference between the weight of the materials in the wet state (Ww) and weight of the materials in the dried state (Wd), according to the following expression: Water content $(\%)=(Ww-Wd)/Wd\times100$; and the capacity of recovery from 60-80% of deformation in 5-15 min and 90-100% of recovery after 3 hours.

The physical properties of spongy-like hydrogels and, per se, their biological performance, can be tuned by simply manipulating the parameters involved in spongy-like hydrogel formation.

The use of bioactive molecules within the spongy-like hydrogels modifies the biological performance of the materials.

The methodology used to obtain gellan gum spongy-like hydrogels involves the subsequent steps of hydrogel preparation, freezing, freeze-drying and re-hydration with any saline solution with/without cells and with/without bioactive molecules.

The preparation of gellan gum hydrogels comprises the dissolution of gellan gum alone or in combination with other(s) in a solvent and the use of a crosslinking mechanism for reticulation.

Gellan gum hydrogels are formed with gellan gum, alone or in combination with other natural/synthetic/modified polymer(s) or co-polymer(s), peptides, proteins, lipids, and polysaccharides, not excluding other molecules. Gellan gum includes, but is not limited to, low-acyl gellan gum, high-acyl gellan gum, chemically modified gellan gum, or any mixture of these gellan gum polymers. Other natural/synthetic/modified polymer(s) or co-polymer(s) includes, but is not limited to, hyaluronate, chitosan, collagen, polyethylene glycol and fibrinogen.

In a preferred embodiment, there is no particular limitation to the polymer concentration, although this should be chosen regarding their viscosity to manufacture the most homogenous hydrogels, at the conditions of polymer(s) dissolution.

In a preferred embodiment, the gellan gum is used in different amounts, from 0.1% (W/V) to 10% (w/v).

In a preferred embodiment, the solvent used to prepare the gellan gum hydrogels is a water based solvent, for instance, water, phosphate buffer solution, etc.

In a preferred embodiment, gellan gum hydrogels are prepared by physical crosslinking, such as thermal and ionic, not excluding other physical or chemical reticulation or the use of other reticulation agents.

In a preferred embodiment, gellan gum hydrogels are prepared by polymer(s) dissolution at temperatures above polymer(s) critical gelling temperature, typically 90° C., for about 10 to 30 min depending on the dissolution of the polymer(s); and by mixing the polymeric solution with the reticulation agent or/and by decreasing the temperature below polymer(s) critical gelling temperature, to promote the polymer crosslinking (reticulation). If using other condition/reticulation agent, this should be added at this stage.

Hydrogels with different shapes can be obtained by adding the solution containing the polymer(s) and crosslinker(s) in specific molds where the polymeric solution gellifies. Hydrogels with different shapes, such as discs, blocks, membranes/sheets/twisted sheets/films, amorphous shape, strips, monoliths, not excluding other shapes, can be obtained.

To obtain hydrogels in the form of fibers, granules, microparticles or beads, the polymeric solution can be loaded in a syringe-like device and dispensed into a reticulation solution. The size of the obtained material, such as the thickness and/or diameter depends on the size of the needle and the volume of polymeric solution dispensed.

In a preferred embodiment, the gellan gum hydrogels are allowed to stabilize in a saline solution to reach their equilibrium swelling state.

In a preferred embodiment, the stabilization saline solution is phosphate-buffered saline solution, not excluding other saline solutions.

In a preferred embodiment, the stabilization in a saline solution occurs from 0 to 48 h, not excluding other stabilization periods.

Gellan gum hydrogels are frozen at temperatures below 0° C., for water and salt cold crystallization.

In a preferred embodiment, hydrogels are frozen during 1 hour to 1 year, more preferably, from 12 h to 44 h, not excluding other freezing periods.

In a preferred embodiment, hydrogels are frozen at temperatures between −4° and −196°, preferably −20° C., −80° C. or −196° C., not excluding other negative temperatures.

Method according to the above description, wherein freezing is performed at different cooling ratios from 0.1° C. per minute to 20° C. per minute.

In a preferred embodiment, the temperature is not altered during the freezing period.

Frozen gellan gum hydrogels are freeze-dried to completely remove all the water.

The time of the freeze-drying process should be sufficient enough to sublime all the water.

In a preferred embodiment, the freeze-drying is performed for one cycle, at −80° C. and 0 atm, for 6 hours to 15 days, preferably for 3-7 days, not excluding other freeze-drying cycles, temperatures, times and pressures.

In a preferred embodiment, the dried polymeric networks obtained from freeze-drying, xerogels, are sterilized. In a more preferred embodiment, the sterilization is made by oxide ethylene, gamma radiation or UV light, not excluding other methods.

In a preferred embodiment, dried polymeric networks are packed and stored off-the-shelf prior use, at controlled humidity and temperature conditions.

The gellan gum dried polymeric networks are re-hydrated at any time with a solvent/solution with/without cells and with/without bioactive molecules.

In a preferred embodiment, the re-hydration is performed with the cell culture medium, not excluding other solutions such as PBS or water, or simulated body fluids (SBF).

In order to obtain a homogenous distribution of the elements to be encapsulated/entrapped/incorporated, a suspension/solution of the designated re-hydration solution, with or without cells and/or bioactive molecules at the desired quantity/concentration, is prepared in a small volume.

In a preferred embodiment the rehydration suspension/solution is administrated on the top of the gellan gum dried polymeric networks forming the gellan gum spongy-like hydrogels.

In a restricted and localized approach, with the possibility of achieving zonal cell and/or bioactive agent entrapment/encapsulation/incorporation on a specific location of the spongy-like hydrogels, the suspension/solution is injected into a specific location of the gellan gum dried polymeric networks structure or of the gellan gum spongy-like hydrogels.

The variety of cells that can be encapsulated/entrapped within the spongy-like hydrogels is quite extent. Different cellular entities, from human or animal origin, such as but not limited to, cell lines, primary cells, progenitor cells, pluri and multipotent stem cells can be entrapped within the spongy-like hydrogels.

Cell lines include, but are not limited to, L929, MRC-5, Saos-2, ATDC5, HeLa, MC3T3, C2C12, MG63, cancer cell lines. Primary cells include, but are not limited to, osteoblasts, fibroblasts, endothelial cells, keratinocytes, epithelial cells, chondrocytes, cardiomyocytes, neurons, melanocytes, smooth muscle cells.

Stem cells include, but are not limited to, hematopoietic stem cells, embryonic stem cells, mesenchymal/stromal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells, pancreatic stem cells, olfactory stem cells, cancer stem cells, induced pluripotent stem cells; and cells differentiated from stem cells and progenitor cells include, but are not limited to epithelial, epidermal and endothelial cells, adipocytes, cardiomyocytes, neurons, osteoblasts, chondrocytes, pancreatic islet cells, retinal cells.

The variety of bioactive molecules that can be encapsulated/entrapped within the spongy-like hydrogels is quite extent. Different bioactive molecules, such as, but not limited to, growth factors, antibodies, antibiotics, anti-microbial, anti-fungi, antimicotics, anti-inflammatory factors, enzymes, metallic elements, growth hormone, cytokines, interleukins, chemokines, angiogenic factors, anti-angiogenic factors, anti-coagulants, contrasting agents, chemotherapeutic agents, signaling pathway molecule, a cell receptor, and cell ligand can be entrapped within the spongy-like hydrogels.

In a preferred embodiment, gellan gum spongy-like hydrogels with entrapped cells are maintained at 37° C., at the optimal humidity and carbon dioxide conditions for in vitro cell culture.

Following, the main advantages of the present invention will be described.

Gellan gum spongy-like hydrogels have cell adhesive character that allows cell encapsulation/entrapment and adhesion, wherein cells maintain their phenotype, without any pre and/or post functionalization with cell adhesive sequences.

All type of cells, comprising cells lineages representative of the three germ layers, can be entrapped, adhere and spread within the spongy-like hydrogels. This phenomena constitutes a major milestone for the biomedical field, enabling the entrapment of functional cells, such as pluri and multipotent stem cells, osteoblasts, keratinocytes, endothelial cells, etc., within a biomaterial.

No pre and/or post functionalization with cell adhesive features, as previously enounced for other hydrogels, is made to prepare spongy-like hydrogels.

The cell adhesive character of gellan gum spongy-like hydrogels, not observed in hydrogels, is in part explained by their physical properties, between sponges and hydrogels, dissimilar from the precursor hydrogels.

The physical properties of the spongy-like hydrogels that are mainly different are the morphology, microstructure, such as porosity and pore size; water content; mechanical performance such as the visco-elasticity, the stiffness, the physical stability, flexibility and recovery capacity.

Considering the clinical application, gellan gum spongy-like hydrogels take advantage relatively to the precursor traditional hydrogels due to the possibility of being available of off-the-shelf materials as dried polymeric networks.

The final step of the preparation of the gellan gum spongy-like hydrogels, which, from a clinical perspective, can be directly compared to the traditional hydrogel preparation with cells and/or bioactive molecules incorporation, is less complex and less time-consuming. Spongy-like hydrogels are prepared through a simple methodology of re-hydration of off-the-shelf materials which comprise long-term stability stored after sterilization.

Gellan gum spongy-like hydrogels also avoid the problematic of the reduced temperature window for reticulation in gellan gum hydrogels that might contribute to a non-homogeneous cell distribution.

Gellan gum spongy-like hydrogels also avoid the use of potentially harsh temperature sat the time of cells encapsulation of cells, which may cause significant cell death.

Gellan gum spongy-like hydrogels can be easily manipulated and transplanted to the patient due to its elastic properties, which facilitates their use by clinicians, in contrast to rigid and easily breakable hydrogels.

The physical properties of spongy-like hydrogels and, per se, their biological performance, can be tuned by simply manipulating the parameters involved in spongy-like hydrogel formation.

As an embodiment of what can be varied at step 1 is the concentration of the polymer(s), the physico-chemical properties of the polymer(s), the type of solvent(s) used for polymer(s) dissolution, and the type, amount and number of crosslinker(s).

As an embodiment of what can be varied at stabilization in saline solution is the time and the ionic solution used for hydrogel stabilization.

As an embodiment of what can be varied at freezing is the type of freezing, such as immersion in liquid nitrogen or freezing in a freezer, the cooling temperature, rate and time.

As an embodiment of what can be varied at freezing-drying is the time, pressure, temperature and cycles of the freeze-drying process, which directly influences the polymeric network arrangement.

The physical properties that can be varied include, but are not limited to, morphology, microstructure, shape, visco-elasticity, stiffness, water absorption, protein adsorption, brittleness, ductility, elasticity, fluidity, viscosity, permeability, plasticity, physical stability, and flexibility.

The biological performance that can be varied or improved include, but is not limited to, cell seeding efficiency, cell spatial control, cell viability, cell proliferation, cell adhesion, cell spreading, cell differentiation and cell signaling.

The variation of the gellan gum spongy-like hydrogel physical properties are also determinant to modulate the bioactive agents which are entrapped, the concentration and the time of their delivery.

All together these characteristics potentiate spongy-like hydrogels application as medical devices and/or as drug delivery systems and/or as scaffolds to be used in cellular tissue regeneration and/or engineering strategies.

Naturally, the present embodiments are not in any way limited to the embodiments described in this document and a person with average knowledge in the field will be able to predict many possible changes to it without deviating from the main idea, as described in the claims.

EXAMPLES

The following examples are provided with a complete disclosure and description of how to make and use the present invention—spongy-like hydrogels. The experiments were not the only experiments performed and are not provided to limit the invention. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, and temperature is in degrees Celsius. Standard abbreviations may be used, e.g., ° C. for Celcius, or sec, second(s); min, minute(s); h or hr, hour(s).

Example 1

As a first example, gellan gum composites spongy-like hydrogels have been defined to be used for bone engineering and repair.

An osteoconductive gellan gum composite spongy-like hydrogel can be made of gellan gum and bioactive glass or/and hydroxyapatite. Stem cells, such as human adipose stem cells can be entrapped within the osteoconductive material, and molecules known to promote osteogenic differentiation, such β-glycerophosphate, ascorbic acid, dexamethasone, as well as growth factors such as bono morphogenetic protein (BMP), transforming growth factor (TGF)-β and vascular endothelial growth factor (VEGF), can also be entrapped within the osteoconductive gellan gum spongy-like hydrogel. The proposed material with entrapped cells and bioactive agents enhance bone tissue formation.

Briefly, gelzan powder (SIGMA, USA) is dissolved in deionized water (1.25% (w/v)), under stirring and at 90° C. Bioactive glass (1% (w/v)) or/and Hydroxyapatite (10% (w/v)) is dissolved in the crosslinking solution containing $CaCl_2$ (0.03% (w/v), VWR, Portugal). After gelzan dissolution, the solution is rapidly mixed with the crosslinking solution and casted into the desired molds, according to the bone defect. The hydrogel is progressively formed until room temperature is reached. Hydrogels are stabilized in PBS for 30 h, then frozen at −80° C. in the freezer for 44 h, and then freeze-dried to obtain dried polymeric networks. A human mesenchymal stem cells suspension ($5\times10^5$ cells and prepared in a volume of 100 μL of the correspondent culture medium) with the bioactive agents, such as BMP (20 $ngml^{-1}$), VEGF (5 $ngml^{-1}$), β-glycerophosphate (10 mM), ascorbic acid (50 $\mu gml^{-1}$), and/or dexamethasone (10 nM), known to promote osteogenic differentiation, is dispensed drop wise on the top of the dried polymeric networks. Constructs are incubated for 30 min, at 37° C., 5% $CO_2$ in the cell culture medium to allow maximum cell entrapment within the structures and then fresh medium is added up to a total volume of 2 mL.

Example 2

As a second example, gellan gum/hyaluronic acid spongy-like hydrogels have been determined to be used for skin engineering.

The main physical properties of spongy-like hydrogels are similar to the properties of the extracellular matrix existing in soft tissues, such as the skin. These materials have the capacity of absorbing and retaining water, higher than gellan gum spongy-like hydrogels due to the incorporation of hyaluronic acid, important to keep the wound moist and for wound exudates absorption. Additionally, due its physical stability, spongy-like hydrogels prevent physical shocks, and due to its mechanical properties, specifically their fast recovery from deformation and elasticity, spongy-like hydrogels can easily adapt to the wound, and not break with the patients' movement. Moreover, since dried polymeric networks can be produced with different shapes, it is possible to produce dressings with specific forms and sizes according to the patient wound. Additionally, spongy-like hydrogels are able to entrap cells from different cell lineages existing in the skin or stem cells which are able to adhere and keep their phenotype within spongy-like hydrogels. Hence, by using confined cell entrapment, different cell types can be entrapped at different depths of the spongy-like hydrogels, enabling to mimic the complexity of skin layers in terms of cellular content.

Briefly, hyaluronic acid (1.5 MDa, LifeCore, USA) is dissolved in deionized water under stirring, at room temperature, for 3 h (0.25% and 0.75% (w/v)). Following, gelzan powder (SIGMA, USA) is added to the hyaluronic acid solution (0.75% and 1.25% (w/v)) and dissolved under stirring and at 90° C. After dissolution, the solutions are casted into the desired molds, according to the patient wound defect, and rapidly mixed with MEM alpha medium crosslinking solution (Life Technologies, Scotland). The hydrogel is progressively formed until room temperature was reached. Spongy-like hydrogels are prepared from these hydrogels following successive steps. Hydrogels are stabilized in PBS for 48 h, then frozen at −80° C. in the freezer for 18-20 h, and then freeze-dried for three days to obtain GG-HA dried polymeric networks. Spongy-like hydrogels are formed after re-hydration of the dried polymeric networks with a cell suspension of each cell type. For cell seeding/entrapment within spongy-like hydrogels, a cell suspension of human adipose stem cells (hASCs) or human adipose stem cells (hASCs) and microvascular endothelial cells (hAMECs)($5 \times 10^5$ cells and prepared in a volume of 100 µL of the correspondent culture medium) is dispensed drop wise on the top the spongy-like hydrogels. Constructs are incubated for 30 min, at 37° C., 5% $CO_2$ to allow maximum cell entrapment within the structures and then fresh medium was added up to a total volume of 2 mL. FIG. 9 shows skin tissue reaction 3 days after transplantation of gellan Gum/hyaluronate spongy-like hydrogels with hASCs alone, and hASCs and hAMECs.

Example 3

As a third example, gellan gum spongy-like hydrogels comprising different microstructures were prepared as drug depots for drug delivery.

Gellan gum spongy-like hydrogels prepared using different processing methodologies presented different physical properties. By using gellan gum spongy-like hydrogels with different microstructures, specifically porosities and pore sizes, different delivery rates can be attained. Hence, fast drug deliveries can be obtained with GG spongy-like hydrogels comprising high porosities and pore sizes (for instance, GG spongy-like hydrogels containing 0.75% of GG, crosslinked with $CaCl_2$, 30 h of stabilization time, −20° C. freezing temperature and 18-20 h of freezing time) while slow deliveries can be achieved with GG spongy-like hydrogels with low porosities and pore sizes (for instance, GG spongy-like hydrogels containing 1.25% of GG, crosslinked with PBS, 30 h of stabilization time, −196° C. freezing temperature and 18-20 h of freezing time).

Briefly, gelzan powder (SIGMA, USA) was dissolved in deionized water (0.75% and 1.25% (w/v)), under stirring and at 90° C. After dissolution, the solutions were casted into the desired molds and rapidly mixed with the crosslinking solution containing mono and/or divalent cations such as $CaCl_2$ (VWR, Portugal), phosphate-buffered saline (PBS, Sigma, USA) or MEM alpha medium (Life Technologies, Scotland). The hydrogel was progressively formed until room temperature was reached. Spongy-like hydrogels were prepared from these hydrogels following successive steps. Hydrogels were stabilized in PBS (2 h and 48 h), then frozen (−196° C. in liquid nitrogen (N2), −20° C. and −80° C. in the freezer for 18-20 h and 42-44 h), and then freeze-dried (LyoAlfa 10/15, Telstar, Spain) for three days to obtain GG dried polymeric networks. Spongy-like hydrogels were formed after re-hydration of the dried polymeric networks.

FIG. 10 shows micro-CT analysis of spongy-like hydrogels with different physical properties.

REFERENCES

Annabi, N., J. W. Nichol, et al. (2010). "Controlling the porosity and microarchitecture of hydrogels for tissue engineering." Tissue Eng Part B Rev 16(4): 371-383.

Chang, H.-I. and Y. Wang (2011). "Cell Responses to Surface and Architecture of Tissue Engineering Scaffolds." Regenerative Medicine and Tissue Engineering—Cells and Biomaterials.

Flory, P. J. (1942). "Thermodynamics of High Polymer Solutions." Journal of chemical physics 10: 59-61.

Holden, A. and P. Morrison (1982). Crystals & Crystal Growing.

Oetjen, G.-W. and P. Haseley (2004). Freeze-drying. Freeze-drying. W.-V. G. C. KGaA.

Oliveira, J. T., L. Martins, et al. (2010). "Gellan gum: a new biomaterial for cartilage tissue engineering applications." J Biomed Mater Res A 93(3): 852-863.

von der Mark, K., J. Park, et al. (2010). "Nanoscale engineering of biomimetic surfaces: cues from the extracellular matrix." Cell Tissue Res 339(1): 131-153.

The invention claimed is:

1. A cell-adhesive gellan gum material, wherein said material is a spongy-like gellan gum hydrogel with a pore diameter between 10 µm and 900 µm, and a mean pore size diameter between 200 µm and 600 µm, a pore wall thickness ranging between 50 µm and 100 µm and a water content between 1000 and 2500% (w/w).

2. The cell-adhesive gellan gum material according claim 1, wherein said material presents a capacity recovery from 60-80% of deformation in 5-15 min and 90-100% of recovery after 3 hours.

3. The cell-adhesive gellan gum material according to claim 1, wherein cells are entrapped and adhered while maintaining their phenotype.

4. The cell-adhesive gellan gum material according to claim 1, wherein bioactive molecules are entrapped.

5. Method for producing the cell-adhesive gellan gum material of claim 1, comprising the following steps:
preparing hydrogel;
freezing, for water and salt cold crystallization;
freeze-drying, to remove all water;
re-hydrating with a solvent or solution.

6. The method according to claim 5, wherein after hydrogel preparation, the hydrogel is stabilized in a saline solution.

7. The method according to claim 5, wherein the gellan gum is selected from the group consisting of low-acyl gellan gum, high-acyl gellan gum, chemically modified gellan gum, and any mixture of these gellan gum polymers.

8. The method according to claim 5, wherein the gellan gum is used in combination with other molecules comprising:
organic molecules selected from the group consisting of polymers of natural or synthetic origin, chemically modified or co-polymers, such as hyaluronate, chitosan, collagen, polyethyleneglicol and fibrinogen, such as peptides, proteins, lipids, and polysaccharides;

inorganic molecules selected from the group consisting of bioactive glass, hydroxyapatite, calcium phosphate and iron.

9. The method according to claim 5, wherein the gellan gum is used in different amounts, from 0.1% (w/v) to 10% (w/v).

10. The method according to claim 5, wherein the hydrogel preparation comprises the dissolution of gellan gum in a solvent and reticulation by a crosslinking mechanism.

11. The method according to claim 10, wherein the solvent comprises water, phosphate buffer solution (PBS), saline solution or cell culture medium.

12. The method according to claim 10, wherein the dissolution of gellan gum occurs at temperatures above polymer(s) critical gelling temperature, preferably at 90° C. and for 10 to 30 minutes.

13. The method according to claim 10, wherein the crosslinking mechanism for reticulation comprises mixing the dissolved gellan gum with a reticulation agent, including ions and decreasing the temperature below the polymers critical gelling temperature.

14. The method according to claim 5, wherein freezing is performed during 1 hour to 1 year, more preferably, during 12 to 44 hours.

15. The method according to claim 5, wherein freezing is performed at a temperature between −4° and −196°.

16. The method according to claim 5, wherein freezing is performed at different cooling ratios from 0.1° C. per minute to 20° C. per minute.

17. The method according to claim 5, wherein the temperature is unaltered during freezing.

18. The method according to claim 5, wherein freeze-drying is performed for one cycle, at −80° C. and at 0 atm, for 6 hours to 15 days, preferably for 3-7 days.

19. The method according to claim 5, wherein rehydration is performed with a polar solvent including water, simulated body fluids (SBF), phosphate buffer solution (PBS) or cell culture medium.

20. The method according to claim 5, wherein rehydration is performed with cell culture medium.

21. The method according to claim 5, wherein re-hydration is performed with one or more types of cells selected from the group consisting of cell lines, primary cells, progenitor cells and stem cells, including human adipose stem cells (hASCs) and microvascular endothelial cells (hAMECs).

22. The method according to claim 5, wherein re-hydration is performed with one or more types of bioactive molecules selected from the group consisting of growth factors, antibodies, antibiotics, anti-microbial, anti-fungi, antimicotics, anti-inflammatory factors, enzymes, metallic elements, growth hormone, cytokines, interleukins, chemokines, angiogenic factors, anti-angiogenic factors, anti-coagulants, contrasting agents, chemotherapeutic agents, signaling pathway molecules, cell receptors, and cell ligands.

23. A method for drug delivery and tissue regeneration and engineering and repair of skin and connective tissues comprising administering the cell-adhesive gellan gum material obtained by the method of claim 5.

* * * * *